United States Patent
Brinker et al.

(10) Patent No.: US 8,903,673 B2
(45) Date of Patent: Dec. 2, 2014

(54) CENTRALLY CONTROLLED MODULAR MOTORIZED TESTING

(75) Inventors: Jeffrey Brinker, Westfield, NJ (US); Wenyu Wang, Pennington, NJ (US)

(73) Assignee: Distek, Inc., New Brunswick, NJ (US)

( * ) Notice: Subject to any disclaimer, the term of this patent is extended or adjusted under 35 U.S.C. 154(b) by 515 days.

(21) Appl. No.: 13/416,024

(22) Filed: Mar. 9, 2012

(65) Prior Publication Data

US 2012/0232824 A1 Sep. 13, 2012

Related U.S. Application Data

(60) Provisional application No. 61/451,826, filed on Mar. 11, 2011.

(51) Int. Cl.
*G06F 19/00* (2011.01)
*G01N 13/00* (2006.01)
*G01N 33/00* (2006.01)
*G01N 35/00* (2006.01)

(52) U.S. Cl.
CPC ............... *G01N 13/00* (2013.01); *G01N 33/00* (2013.01); *G01N 2013/006* (2013.01); *G01N 2035/00198* (2013.01)
USPC ........... 702/108; 73/866; 73/53.01; 422/68.1; 220/23.87; 366/241; 366/244

(58) Field of Classification Search
CPC ..................... G01N 13/00; G01N 2035/00198; G01N 2013/006; G01N 33/15
USPC ........... 702/108; 73/64.56, 864.9, 866, 53.01; 422/68.1, 64; 220/23.87; 366/241, 242, 366/244, 143, 273, 274
See application file for complete search history.

(56) References Cited

U.S. PATENT DOCUMENTS

| | | | | |
|---|---|---|---|---|
| 4,879,917 A | * | 11/1989 | Eppelmann et al. | 73/866 |
| 5,412,979 A | * | 5/1995 | Fassihi | 73/53.01 |
| 5,586,305 A | | 12/1996 | Eidson et al. | |
| 5,589,649 A | * | 12/1996 | Brinker et al. | 73/866 |
| 5,682,001 A | * | 10/1997 | Hanson et al. | 73/866 |
| 5,809,224 A | | 9/1998 | Schultz et al. | |
| 6,060,024 A | * | 5/2000 | Hutchins et al. | 422/81 |
| 6,262,550 B1 | | 7/2001 | Kliman et al. | |
| 6,303,909 B1 | * | 10/2001 | Fernando et al. | 219/429 |

(Continued)

FOREIGN PATENT DOCUMENTS

WO WO 9523329 A1 * 8/1995

*Primary Examiner* — Carol S Tsai
(74) *Attorney, Agent, or Firm* — Mendelsohn, Drucker & Dunleavy, P.C.; Edward J. Meisarosh; Steve Mendelsohn

(57) ABSTRACT

In one embodiment, a modular dissolution-testing apparatus has a base unit adapted to hold and control operation of between one and eight dissolution-testing modules. The base unit has a programmable controller and a color touch screen for user interface with the controller and the modules. Each module includes a vessel for holding a solution of a dosage form dissolving in a solvent, an agitator apparatus for stirring the solution, and a motor to power—via a multi-motion assembly and a stirring shaft—stirring by, lifting of, and lowering of, the apparatus. Each module has a vessel heater and a temperature sensor, both communicatively connected to the controller for heating and regulating the temperature of the vessel contents. Each module is independently controllable by the controller, where control includes manually (by a user) or programmatically setting stirring speed, lifting and lowering apparatus, and starting and stopping stirring and heating.

21 Claims, 8 Drawing Sheets

(56) References Cited

U.S. PATENT DOCUMENTS

| | | |
|---|---|---|
| 6,535,786 B1 | 3/2003 | Duemler |
| 6,727,480 B2 * | 4/2004 | Fernando et al. ............ 219/549 |
| 6,825,860 B1 | 11/2004 | Hu et al. |
| 6,901,316 B1 | 5/2005 | Jensen et al. |
| 6,938,435 B2 * | 9/2005 | Goseling et al. ............. 62/342 |
| 6,962,674 B2 * | 11/2005 | Dean et al. ................. 422/68.1 |
| 6,970,986 B1 * | 11/2005 | Mahmoud .................... 711/158 |
| 7,050,943 B2 | 5/2006 | Kauffman et al. |
| 7,469,708 B2 * | 12/2008 | Koester ........................ 137/269 |
| 7,495,726 B2 * | 2/2009 | Chen ............................ 349/114 |
| 7,585,465 B2 * | 9/2009 | Lee et al. .................... 422/68.1 |
| 7,668,605 B2 | 2/2010 | Braun et al. |
| 7,882,275 B2 | 2/2011 | Fredriksson et al. |
| 7,914,741 B2 * | 3/2011 | Williams et al. ............ 422/68.1 |
| 7,938,032 B2 * | 5/2011 | Fernando .................... 73/865.6 |
| 8,430,257 B2 * | 4/2013 | Fetvedt et al. ............ 220/23.87 |
| 8,511,148 B2 * | 8/2013 | Fetvedt ....................... 73/64.56 |
| 2002/0119076 A1 * | 8/2002 | Dean et al. ................. 422/68.1 |
| 2004/0247489 A1 * | 12/2004 | Fernando et al. ............ 422/100 |
| 2006/0260422 A1 * | 11/2006 | Sekizawa et al. .............. 73/866 |
| 2008/0226499 A1 * | 9/2008 | Williams et al. ................ 422/64 |
| 2009/0155936 A1 * | 6/2009 | Weiner et al. ................... 438/17 |

\* cited by examiner

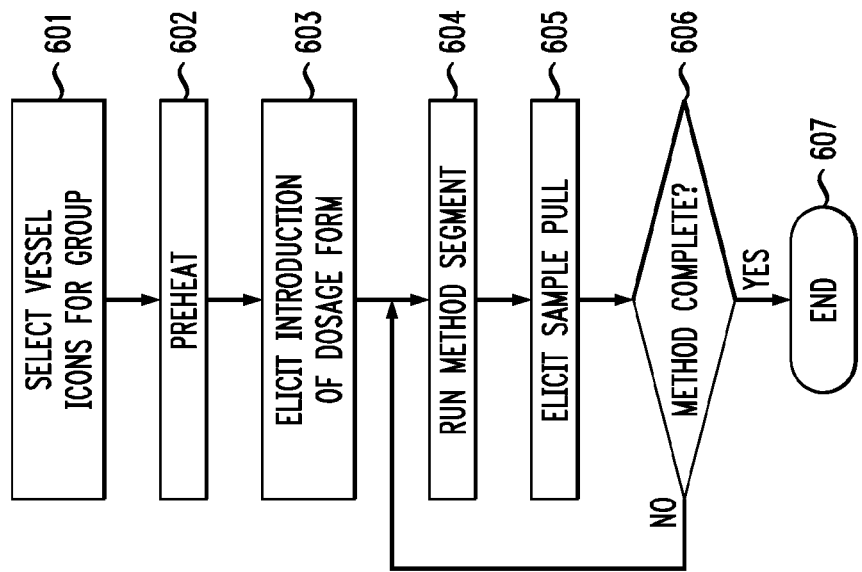
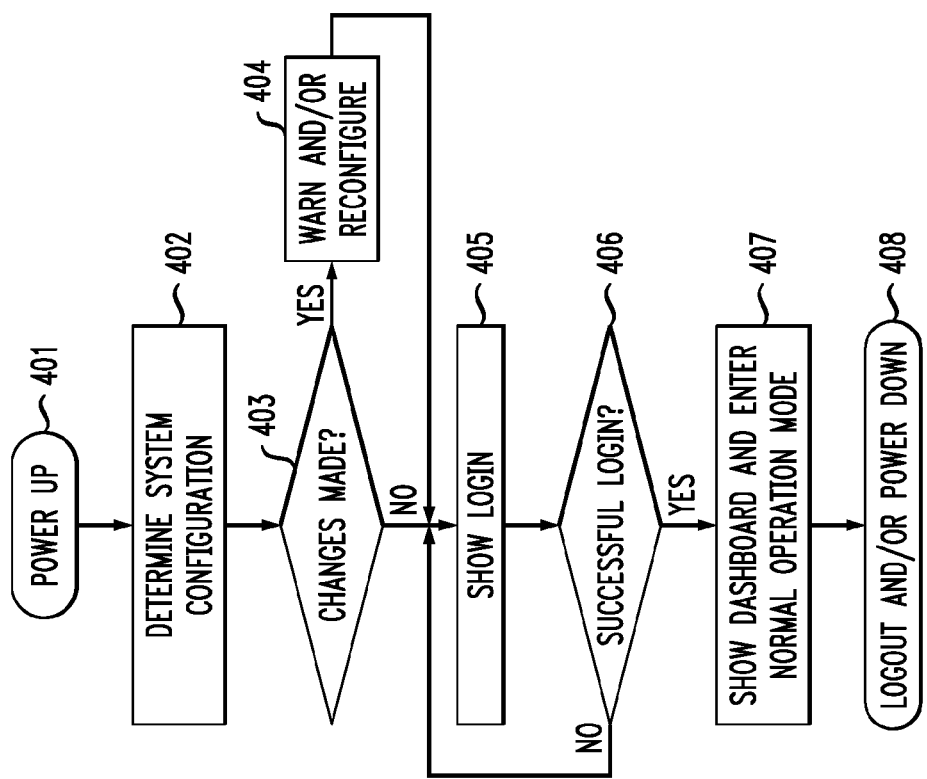

FIG. 8
500

DISTEK  ●◍○                                       12:00 AM  JANUARY 1, 2010

| DASHBOARD | TEST DETAILS | REPORTS | SETTINGS | LOGOUT |

REPORT SUMMARY                    TEMP 00.0°C     RPM 000     APP BASKET  VOL 000ml
ADMINISTRATOR                     STARTED 01/01/10 12:00AM    COMPLETE 12/31/10 11:59PM

| VESSEL | TEMPERATURE (°C) | | | RPM | | |
|        | LAST | MIN | MAX | DELTA | LAST | MIN | MAX | DELTA |
|--------|------|-----|-----|-------|------|-----|-----|-------|
| ONE    | 37.00 | 37.00 | 37.00 | 0.0 | 50.00 | 50.00 | 50.00 | 0.0 |
| TWO    | 37.00 | 37.00 | 37.00 | 0.0 | 50.00 | 50.00 | 50.00 | 0.0 |
| THREE  | 37.00 | 37.00 | 37.00 | 0.0 | 50.00 | 50.00 | 50.00 | 0.0 |
| FOUR   | 37.00 | 37.00 | 37.00 | 0.0 | 50.00 | 50.00 | 50.00 | 0.0 |
| FIVE   | 37.00 | 37.00 | 37.00 | 0.0 | 50.00 | 50.00 | 50.00 | 0.0 |
| SIX    | 37.00 | 37.00 | 37.00 | 0.0 | 50.00 | 50.00 | 50.00 | 0.0 |
| SEVEN  | 37.00 | 37.00 | 37.00 | 0.0 | 50.00 | 50.00 | 50.00 | 0.0 |
| EIGHT  | 37.00 | 37.00 | 37.00 | 0.0 | 50.00 | 50.00 | 50.00 | 0.0 |

[PRINT]                                                                  [BACK]

CENTRALLY CONTROLLED MODULAR MOTORIZED TESTING

This application claims the benefit of the filing date of U.S. Provisional Application No. 61/451,826 filed on Mar. 11, 2011, the teachings of which are incorporated herein by reference in their entirety.

BACKGROUND OF THE INVENTION

1. Field of the Invention

The current invention relates to systems and methods for controlled motorized operations, and more specifically, but not exclusively, to systems and methods for centrally controlled modular and scalable motorized scientific instrumentation.

2. Description of the Related Art

Dissolution testing apparatuses are controlled motorized testing systems used to determine the dissolution rates of solutes, such as pharmaceutical pills—also known as solid oral dosage forms, in specific solvents and at specified temperatures. This type of testing procedure is used, for example, in quality assurance (QA) dissolution testing—so-called since it is used to determine aspects of pharmaceutical quality—and in research and development (R&D). In dissolution testing, a dosage form (e.g., pill, tablet, or capsule) is typically either (1) dropped into a solvent-containing vessel, where a paddle is used to stir the solution that results from the dissolution of the solute in the solvent or (2) placed in a cage-like basket which is lowered into the solvent and spun, thereby also stirring the resultant solution. A test method specifies various dissolution test parameters, such as the stirring apparatus (e.g., paddle or basket), stirring speed (e.g., in revolutions per minute (RPM)), and the solution temperature. Samples of the solution are pulled at specified intervals during the test method run. These samples are then tested to determine the extent of dissolution of the dosage form at the specified time intervals.

Conventional dissolution testing systems are made in the form of a unitary integrated apparatus comprising six, seven, or eight vessels and corresponding stirring apparatuses for holding and stirring corresponding solutions of solvent and solute. The multiple stirring apparatuses are typically powered by a single motor to which they are connected by, for example, belts or gear systems. Industry practice for QA dissolution testing is to run six identical tests simultaneously in order to provide sufficient data for standard statistical analysis of the data. In other words, conventional apparatuses have six vessels whose contents are (1) at the same temperature and (2) stirred at the same speed by the same kind of stirring apparatus. The seventh and/or eighth vessel in dissolution testing apparatuses that have seven or eight vessels are typically used to provide replacement solvent at the proper temperature to replace the solution removed from the first six vessels in sample pulls. The temperature of the solution in a vessel may be maintained by (1) placing the vessel in a temperature-controlled water bath or (2) using a heating jacket around the vessel, as in a bathless apparatus.

SUMMARY OF THE INVENTION

One embodiment of the invention can be a detachable module usable for scientific testing, the detachable module adapted to attach to, and detach from, a corresponding attachment bay of a base unit. The base unit comprises a controller. The detachable module comprises (i) a first connection port adapted to support communication with the controller, the first connection port adapted to connect to a corresponding connection port of the corresponding attachment bay when the detachable module is attached to the base unit, (ii) a first sensor adapted to provide a first output to the controller via the first connection port, and (iii) an agitator apparatus adapted to agitate a medium, and be controlled by the controller via the first connection port.

Another embodiment of the invention can be an apparatus usable for scientific testing, the apparatus comprising a base unit. The base unit comprises a plurality of attachment bays, a user interface, and a controller communicatively connected to the user interface. Each of the plurality of attachment bays (a) is adapted to have a corresponding detachable module attach to, and detach from, the attachment bay and (b) comprises a first connection port adapted to (i) connect to a corresponding connection port of the corresponding detachable module, (ii) support communication between the corresponding detachable module and the controller when the corresponding detachable module is attached to the attachment bay, (iii) transmit a first output from a sensor in the corresponding detachable module to the controller, and (iv) support control by the controller of an agitator apparatus in the corresponding detachable module, wherein the agitator apparatus is adapted to agitate a medium.

Yet another embodiment of the invention can be a method for scientific testing using an apparatus. The apparatus comprises a first detachable module and a base unit. The first detachable module comprises (a) a sensor, (b) an agitator apparatus adapted to agitate a medium, and (c) a first connection port. The base unit comprises (a) a plurality of attachment bays, (b) a user interface, and (c) a controller communicatively connected to the user interface. Each of the plurality of attachment bays (i) is adapted to have a corresponding detachable module attach to or detach from the attachment bay and (ii) comprises a corresponding connection port. The first detachable module is attached to a first attachment bay of the plurality of attachment bays. The first connection port of the first detachable module is connected to the corresponding connection port of the first attachment bay. The method comprises (a) communicating, by the controller, with the first detachable module via the first connection port, (b) receiving, by the controller, a first output from the sensor in the first detachable module, and (c) controlling, by the controller, of the agitator apparatus in the first detachable module.

Yet another embodiment of the invention can be an apparatus usable for scientific testing. The apparatus comprises a user interface, a controller communicatively connected to the user interface, and a plurality of testing modules. Each of the plurality of testing modules comprises a first sensor adapted to provide a first output to the controller, an agitator apparatus adapted to agitate a medium and be controlled by the controller. The controller is adapted to simultaneously provide a first set of control instructions to a first set of one or more of the plurality of testing modules and provide a second set of control instructions, different from the first set of control instructions, to a second set of one or more of the plurality of testing modules, different from the first set of one or more of the plurality of testing modules.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 4 shows a flowchart showing exemplary operation of the apparatus of FIG. 1 in accordance with one embodiment of the invention.

FIG. 6 shows a flowchart showing an exemplary method-run operation of the apparatus of FIG. 1 in accordance with one embodiment of the present invention.

FIG. 8 shows the exemplary operations window of FIG. 5, after selecting the reports tab and a completed method.

DETAILED DESCRIPTION

Described below is an embodiment of the invention, implemented as a centrally controlled modular dissolution-testing apparatus having a base unit with a controller and one or more dissolution-testing modules, each module having one vessel. Using a scalable, centrally controlled modular dissolution-testing apparatus can provide various advantages over the conventional unitary integrated apparatus. Users who require a dissolution testing system having fewer than six vessels will be able to have such a system and possibly incur reduced costs. If the user's needs grow, additional dissolution-testing modules may be added as needed. If a single dissolution-testing module of the modular system breaks down, replacement of the single module would be simpler, faster, and cheaper than the repair or replacement of an entire unitary multi-vessel system. Furthermore additional novel features of a central controller, which are described below, add convenience and utility to the modular dissolution-testing apparatus.

Figure 1:
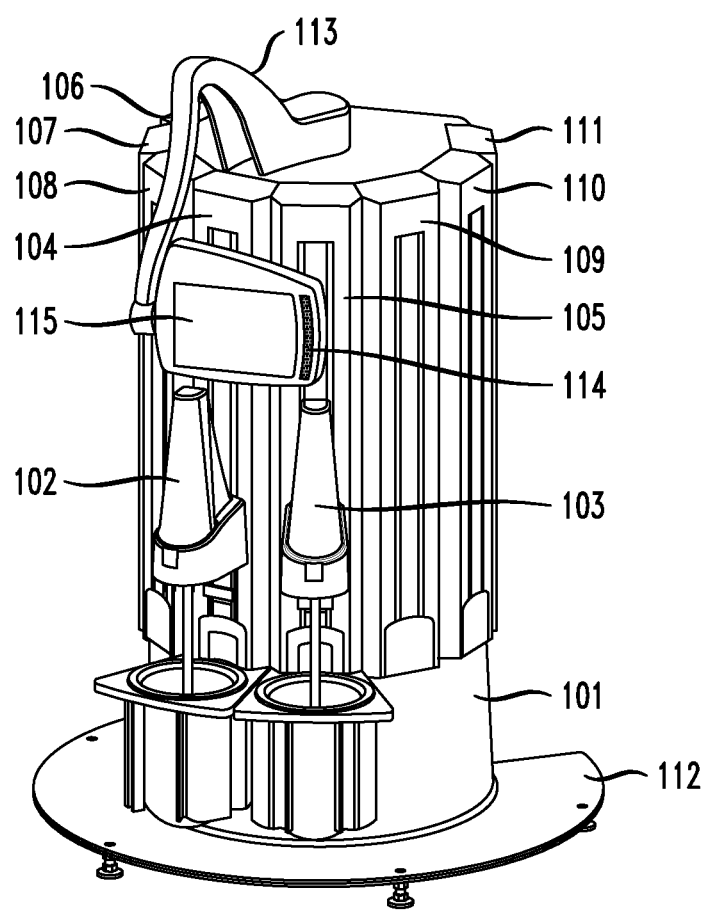
FIG. 1 shows a perspective view of a modular dissolution testing apparatus in accordance with one embodiment of the present invention.

FIG. 1 shows a perspective view of modular dissolution-testing apparatus 100 in accordance with one embodiment of the present invention. Apparatus 100 is scalable for use with one to eight detachable dissolution-testing modules. Apparatus 100 comprises base unit 101, detachable dissolution-testing modules 102 and 103—having corresponding covers 104 and 105, respectively—and unused-attachment-bay covers 106, 107, 108, 109, 110, and 111. Base unit 101 is shaped substantially as a vertical tower having a deformed-cylinder cross section with supportive base plate 112. Base unit 101 comprises eight contiguous attachment bays along part of its periphery, which are substantially horizontal receptacles adapted to hold in place corresponding detachable dissolution-testing modules (such as, for example, modules 102 and 103) or unused-attachment-bay covers. Each attachment bay includes a connection port (not shown) for interfacing with an attached dissolution-testing module. As suggested above, base unit 101 can accommodate up to six additional dissolution-testing modules in addition to modules 102 and 103, for a total of eight modules. To connect an additional dissolution-testing module, one removes an unused-attachment-bay cover, such as cover 109, and inserts and connects the module into the corresponding attachment bay. Dissolution-testing modules 102 and 103 and unused-attachment-bay covers 106, 107, 108, 109, 110, and 111 are secured to their respective attachment bays with screws.

Base unit 101 also comprises a controller (not shown). The controller comprises a processor and a communicatively connected memory usable to store program code, parameters, measurements, and other useful information. Base unit 101 additionally comprises circuitry to communicatively connect the controller to various elements of apparatus 100, such as, for example, the connection ports of the attachment bays and/or a serial communication port (e.g., RS-232 or USB) for interfacing with an external computer.

Base unit 101 further comprises armature 113, which has a first end rotatably connected to the top of base unit 101, and user interface 114, which is movably connected to a second end of armature 113. User interface 114 is a structure comprising touch screen 115 communicatively connected to the controller. User interface 114 may include a user-interface controller (not shown) communicatively connected to the controller of base unit 101 and to touch screen 115. The attachments of user interface 114 to armature 113 and of armature 113 to base unit 101 are such that a user can easily (i.e., without much physical effort) move and reorient touch screen 115 and have touch screen 115 remain substantially in its new position until moved again.

Figure 2:
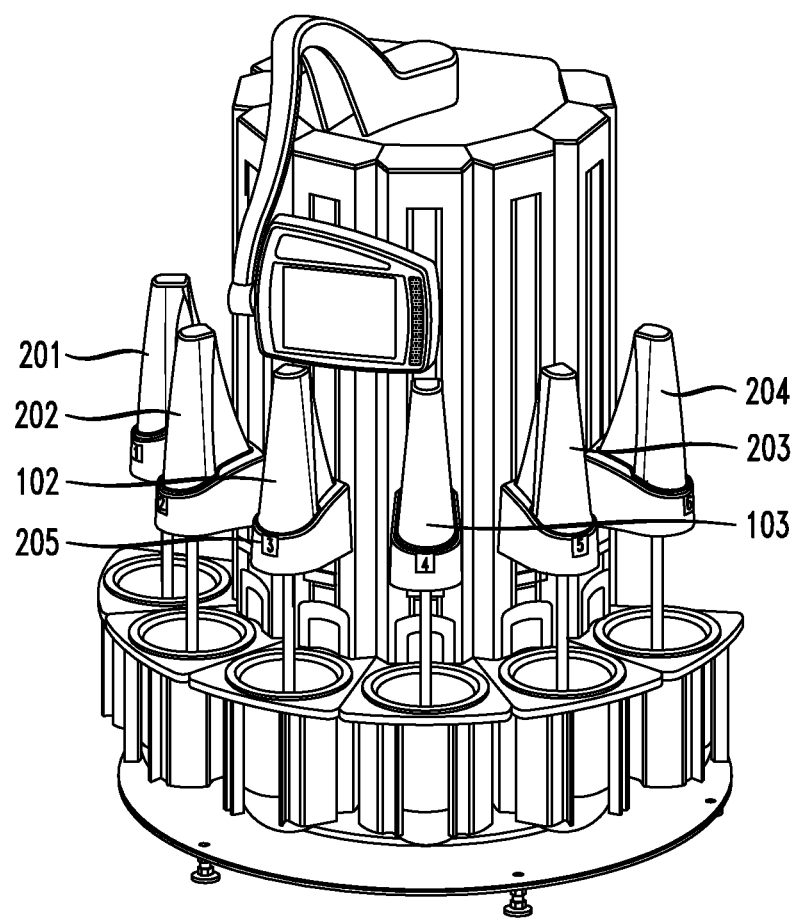
FIG. 2 shows a perspective view of the dissolution testing apparatus of FIG. 1, but with six dissolution testing modules.

FIG. 2 shows a perspective view of dissolution-testing apparatus 100 of FIG. 1, but with six detachable dissolution-testing modules. Namely, in addition to modules 102 and 103, apparatus 100 in FIG. 2 also comprises modules 201, 202, 203, and 204, which now stand in place of covers 107, 108, 109, and 110, respectively. Other elements of apparatus 100 are substantially the same as in FIG. 1. The modules may be labeled with unique and visible identifiers—such as sequential integer numbers (e.g., label 205 on module 102, showing the number "3")—to correlate respective dissolution-testing modules and/or components therein with their corresponding iconic representations on touch screen 115. Note that the deformed-cylinder (almost semi-circular) footprint of base unit 101 allows for easy access to each and all of the dissolution-testing modules from just one side.

Figure 3:
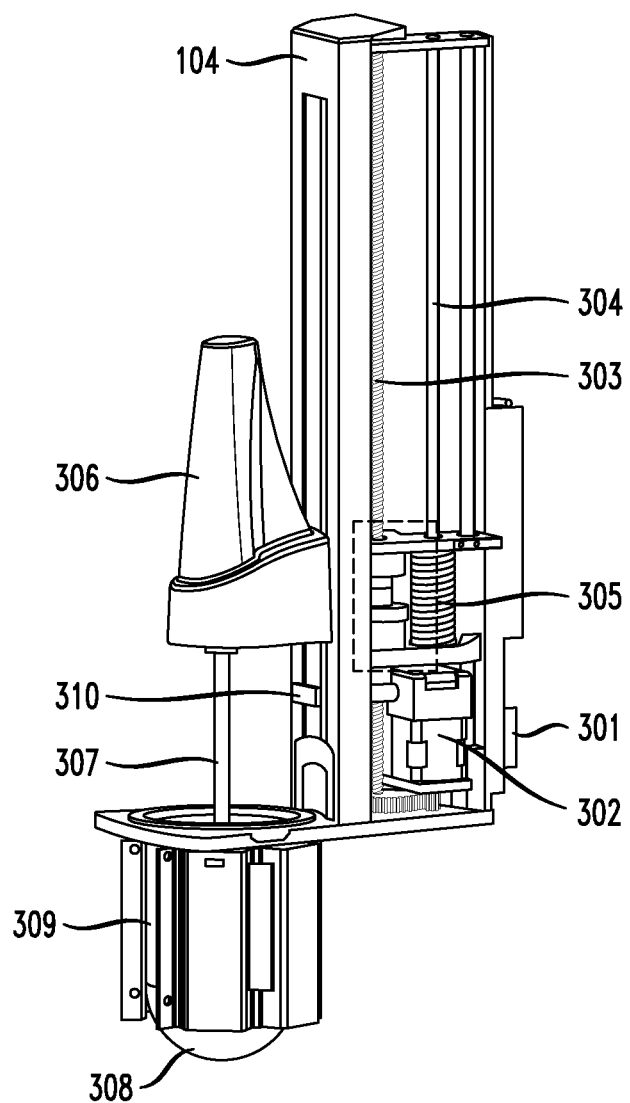
FIG. 3 shows a perspective view of a dissolution-testing module of FIG. 1—disconnected from the base unit.

FIG. 3 shows a perspective view of dissolution-testing module 102 of FIG. 1—disconnected from base unit 101. Note that the description below for dissolution-testing module 102 also applies to other dissolution-testing modules, such as modules 103, 201, 202, 203, and 204 of FIG. 2. Dissolution-testing module 102 connects electronically to base unit 101 via connection port 301, which—when module 102 is inserted in base unit 101—connects to the connection port in the corresponding attachment bay of base unit 101 for the receipt of electrical power from base unit 101 and for communication between module 102 and the controller of base unit 101. Connection port 301 may be in the form of a standard computer peripheral component interconnect (PCI) card, where the corresponding connection port of the attachment bay is a corresponding PCI slot. Module 102 also comprises motor 302, leadscrew 303, guide rod 304, multi-motion assembly 305 (indicated by the dashed rectangle in the figure), bearing assembly 306, stirring shaft 307, dissolution vessel 308, heating jacket 309—for heating the contents of dissolution vessel 308, and a temperature sensor (not shown)—for sensing the temperature of the contents of dissolution vessel 308. The temperature sensor may be embedded inside stirring shaft 307. Dissolution-testing module 102 may also comprise a stirring-speed sensor for providing stirring-speed feedback to the controller.

Leadscrew 303 is adapted to be rotationally powered by motor 302. Guide rod 304 is substantially parallel to leadscrew 303. Dissolution-testing module 102 may include additional guide rods. The guide rods are used to provide stability to dissolution-testing module 102 and guide the motion of multi-motion assembly 305 and the attached bearing assembly 306, which comprises one or more bearings—connected to be indirectly powered by motor 302—for holding and providing rotational power to stirring shaft 307. The end of stirring shaft 307 that is adapted to be inserted into vessel 308 may be fitted with any one of various agitator attachments such as, for example, a paddle or a basket (not shown).

Multi-motion assembly 305 may be in the form of the D-Drive technology of the Symphony 7100 Dissolution Test System from Distek, Inc., of North Brunswick, N.J. Multi-motion assembly 305 includes a clutch mechanism that selectively uses the rotation of leadscrew 303 to have multi-motion assembly 305 either (a) move up or down leadscrew 303—together with bearing assembly 306 and stirring shaft 307—or (b) stay in place and power the rotation of stirring shaft 307—via bearing assembly 306—once the attachment on stirring shaft 307 is lowered to a predetermined position inside vessel 308.

The controller of base unit 101 may control the speed (i.e., RPM) of the motor, thereby controlling the speed at which (a) multi-motion assembly 305, together with bearing assembly 306 and stirring shaft 307, move up or down leadscrew 303 and (b) stirring shaft 307 and any attached agitator apparatus rotate (such as when stirring shaft 307 stirs the contents of vessel 308 with an attached paddle).

Dissolution-testing module 102 also comprises a brake pad and brake-pad locator 310. The location of the brake pad along leadscrew 303 determines the lowest level to which multi-motion assembly 305 can descend and the level at which its clutch mechanism causes a shift from up/down motion to stirring-shaft rotation. In other words, when multi-motion assembly 305 is moved down and pressed against the brake pad, the clutch mechanism shifts so that continued rotation of leadscrew 303 causes stirring shift 307 to rotate. Reversing direction of leadscrew 303 causes (1) the stirring to stop and (2) multi-motion assembly 305 to rise. The user may set the location of brake-pad locator CK—and the corresponding brake pad—to set the height at which the stirring-shaft attachment is set to rotate. Cover 104 may be marked with one or more pre-set locations for brake-pad locator 310 for one or more corresponding standard test methods that require particular locations for paddles or baskets within vessel 308 during dissolution testing.

Heating jacket 309 comprises heating elements (not shown) for providing heat to vessel 308 and its contents. Any type of heating elements (e.g., resistance wires) may be used by heating jacket 309. The temperature sensor is used by the controller in a negative feedback loop to allow for the setting of one or more precise operating temperatures for the contents of vessel 308, where the operating temperature may be rapidly reached and then stabilized. A typical operating temperature for the contents of vessel 308 is 37 degrees Celsius. The operating temperature is controlled by the controller of base unit 101.

The controller of base unit 101 of FIG. 1 can control any set of connected dissolution-testing modules. In other words, the controller may specify operation of a single dissolution-testing module or of one or more different subsets of a plurality of dissolution-testing modules. When controlling multiple modules, the controller may independently control each of the modules. In other words, the controller may have stirring shafts of a first subset of dissolution-testing modules stirring at a first speed and temperature, a second subset stirring at a second speed and temperature, a third subset raising or lowering their multi-motion assemblies, and a fourth subset standing idle. The independent control may be used to run multiple different test methods simultaneously on apparatus 100. The controller may record sensed dynamic information such as, for example, temperature and/or stirring speed, at particular time intervals.

A user may interact with the controller—e.g., give commands and receive feedback—via touch screen 115. Operations specified by the controller can be for immediate execution or for time-delayed execution—as in, for example, programmed test methods. As described above, the controller receives sensor input, such as temperature, and, in turn, implements method parameters such as, for example, stirring speed (from zero to maximum speed) and heater setting. The controller can also perform additional tasks such as, for example, controlling lights to identify or illuminate particular dissolution-testing modules. The controller may detect the presence of modules upon connection to their corresponding connection ports in the attachment bays or during a power-up routine. The controller may receive corresponding IDs from the dissolution-testing modules via the connection ports.

Apparatus 100 may be set to automatically perform a pre-programmed procedure upon the detection of the insertion or removal of one or more dissolution-testing modules. For example, if the number of modules is changed to x, then apparatus 100 may automatically reconfigure to operate as an x-vessel system. Apparatus 100 may also be set to require a technician's intervention to reprogram apparatus 100 to operate with a different number of modules. Requiring reconfiguration by a technician may be useful to prevent unauthorized modifications that may be unsafe. Requiring a technician's intervention for reconfiguration, or other actions, may be implemented by, for example, (1) requiring the entry of an authorization code on touch screen 115 or (2) the use of a hardware key (not shown) in an electro-mechanical switch (not shown) in base unit 101 that is communicatively connected to the controller to indicate engagement of the switch by the hardware key.

As noted above, a user may interact with the controller via touch screen 115. Touch screen 115 is a color touch screen, which allows for a more-varied and useful visual output to the user than a black-and-white touch screen. In addition to control of the dissolution-testing modules, the controller offers method and report storage, and multiple user-access levels to improve users' command and productivity. Touch screen 115 of FIG. 1 provides users with an interactive interface for controlling and monitoring apparatus 100. Features include storing and running methods, storing reports, managing a plurality of users at different access levels, and performing apparatus maintenance. Features of the controller, as accessed via touch screen 115, are described below. Note that, unless otherwise indicated, user input to the controller and controller output to the user is performed through touch screen 115.

FIG. 4 shows flowchart 400 showing exemplary operation of apparatus 100 of FIG. 1 in accordance with one embodiment of the invention. Touch screen 115—and apparatus 100 generally—may be turned on with a power button (not shown) (step 401). Note that apparatus 100 may be powered down using the power button or by selecting a shut-down option on touch screen 115. Upon power-up, a startup check is performed by the controller to determine system configuration and status (step 402). The controller determines which attachment bays have dissolution-testing modules—or other compatible modules—attached to base unit 101 and may get identification information—such as a module serial number—from each one. The controller may compare the identification information to a stored list of identifiers to determine if any changes have been made (step 403). If changes are detected, then the controller may provide the user a warning or may offer a reconfiguration option (step 404). Next, touch screen 115 shows a login screen for user login (step 405). The login screen may have a text-entry box for typing in a user name or a selection box (e.g., drop-down or scrollable list) for selecting a user identifier (e.g., name). Touch screen 115 may show a corresponding access level for each user. After a user identifier is entered or selected, the user may be prompted to enter a corresponding passkey in a text-entry box or on a keypad.

If the login is successful (step 406), then touch screen 115 shows an operations window—described below—and enters normal operation mode, which allows user interaction with apparatus 100 at a level that corresponds to the user's access level (step 407). The operations window is a multi-tab screen that starts on the dashboard tab, described below. If login is unsuccessful (step 406), then touch screen 115 returns to step 405—showing the login screen. When a user is done with a session, the user may log out and/or power down apparatus 100 (step 408). Note that if a test method is running, then the logout and shutdown options are made unavailable to the user. Unavailability of options generally may be indicated by, for example, graying out the corresponding buttons on touch screen 115, deleting them, or otherwise changing their visual appearance on touch screen 115. Note that mechanisms may be provided to allow certain users to log out and/or power down apparatus 100 even if a test method is running.

Figure 5:
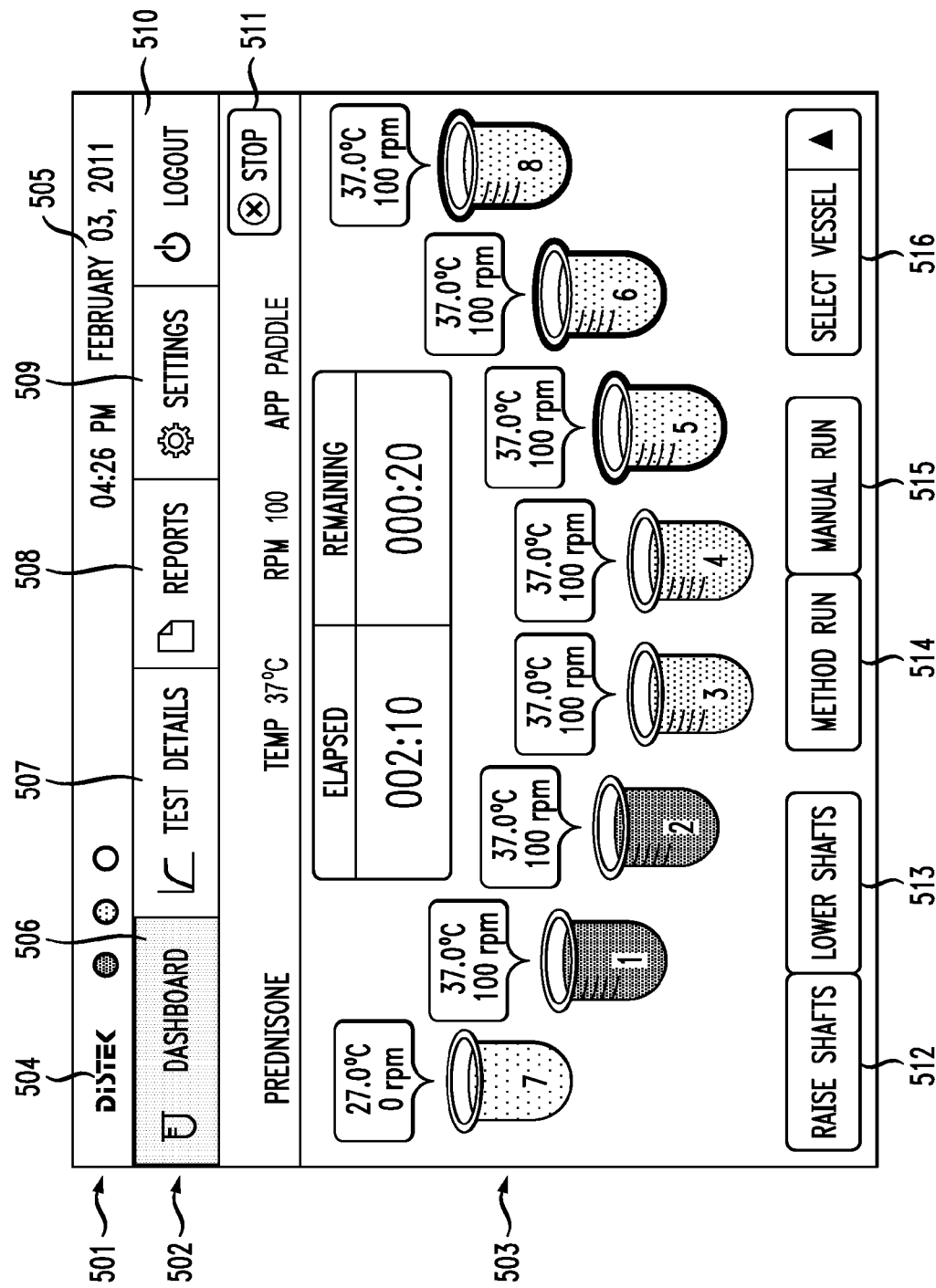
FIG. 5 shows an exemplary operations window on the touch screen of FIG. 1, after selecting a dashboard tab.

FIG. 5 shows exemplary operations window 500 on touch screen 115 of FIG. 1, after selecting a dashboard tab. Operations window 500 comprises status ribbon 501 on top, tab-select ribbon 502 underneath status ribbon 501, and tab-info window 503 underneath tab-select ribbon 502. Status ribbon 501 includes (1) provider logo 504, showing the logo of Distek, Inc., of North Brunswick, N.J., and (2) time and date info 505. Tab-select ribbon 502 shows (1) dashboard tab 506 as selected and (2) test-details tab 507, reports tab 508, settings tab 509, and logout tab 510 as unselected but available. Tab-info window 503 shows information for the selected tab. Specifically, tab-info window 503 shows information for apparatus 100, including which attachment bays hold a corresponding dissolution-testing module—indicated by corresponding vessel icons identified by integer numbers—and sensed vessel temperature and stirring-shaft speed (in RPM) for the connected dissolution-testing modules. Note that, as described above, the corresponding modules and/or vessels may be labeled with conforming numbers.

When one or more test methods are running, tab-info window 503 shows information, for a selected method, such as (1) method name or title (e.g., "Prednisone"), (2) method parameters such as (a) target temperature (e.g., 37° C.), (b) target stirring speed (e.g., 100 RPM), and (c) agitator apparatus (e.g., paddle) attached to the stirring shaft, and (3) temporal status, such as, for example, (a) method time elapsed and (b) time remaining until a next scheduled event (e.g., a sample pull). Note that a stirring speed may also be indicated, for example, as a fraction or percentage of a maximum speed. Note that if a method is running on only a subset of attached dissolution-testing modules (e.g., modules 5, 6, and 8), then those modules may be indicated by highlighting (e.g., outlining in bold).

If subsets of dissolution-testing modules are being used differently (e.g., running different test methods), then the different subsets may be identified by using corresponding colors for the vessel icons, where one color is used for all members of one subset and different colors are used for the other subsets. Different shadings, brightness levels, or fill patterns may be used instead of, or in addition to, colors. Exemplary tab-info window 503 shows vessels 5, 6, and 8 as belonging to one three-module group (as well as highlighted, as noted above), vessels 1 and 2 as belonging to a two-module group, and vessels 3 and 4 belonging to another two-module group. Tab-info window 503 shows vessel 7 as grayed out and at zero RPM, indicating that the corresponding dissolution-testing module is idle.

Tab-info window 503 also includes buttons such as (1) stop button 511 for stopping a running method, (2) raise-shafts button 512 for raising the shafts of a selected group of dissolution-testing modules, (3) lower-shafts button 513 for lowering the shafts of a selected group of dissolution-testing modules, (4) method-run button 514 for running a selected method, (5) manual-run button 515 for manually controlling operation of selected dissolution-testing modules, and (6) select-vessels button 516 for selecting a set of vessel icons. Note that, if a test method is running on a group of dissolution-testing modules, then selecting the vessel icon of any dissolution-testing module in the group may select the entire group. As noted above, under certain circumstances, any number of buttons or options may be disabled but visible, where the disability may be indicated by having the button or option grayed out. For example, raise-shafts button 512 and lower-shafts button 513 may be available in manual mode but not while a method is running. Also note that similar buttons may function differently in different circumstances. For example, pressing stop button 511 in manual mode will stop the stirring in the selected dissolution-testing modules rather than stop a method.

FIG. 6 shows flowchart 600 showing an exemplary method-run operation of apparatus 100 of FIG. 1 in accordance with one embodiment of the present invention. Once a method to be run is selected, the method run starts with the selection of the vessel icons for the dissolution-testing modules that will run the method (step 601). After all the modules are selected, the user indicates readiness for the next phase and the method starts with a preheat phase (step 602), in which the vessel contents are heated to a specified temperature. During the preheat, tab-info window 503 of FIG. 5 may show "preheat" rather than a particular time remaining until a next scheduled event. Once the appropriate temperature has been reached, tab-info window 503 shows the corresponding vessel icons as flashing. In addition, user interface 114 may sound a corresponding audible alert using a speaker or other sound generator (not shown).

Depending on method parameters (e.g., whether the method uses a paddle or a basket, whether dosage forms are introduced into the various vessels simultaneously or in a staggered drop), the user is instructed to appropriately introduce dosage forms into the corresponding vessels (step 603). The dosage forms may also be introduced automatically using an appropriate automatic dosage-form dispenser (not shown). After the dosage forms are introduced, the method run is started and a method segment is run (step 604). The start may be simultaneous for the corresponding dissolution-testing modules or staggered by vessel. When it is time to pull a sample, the corresponding vessel icons are highlighted and a corresponding audible alert may be sounded (step 605). Icon highlighting may be indicated by, for example, flashing the icon and/or altering it to add a cannula icon. Samples may also be pulled automatically by, for example, using an autosampler (not shown). Note that, if solvent is to be replaced at set intervals, then those intervals may be indicated in a similar manner. If the method is completed (step 606), then the method run terminates (step 607); otherwise, the method run continues as above with another method segment (step 604) until the next sample pull.

Figure 7:
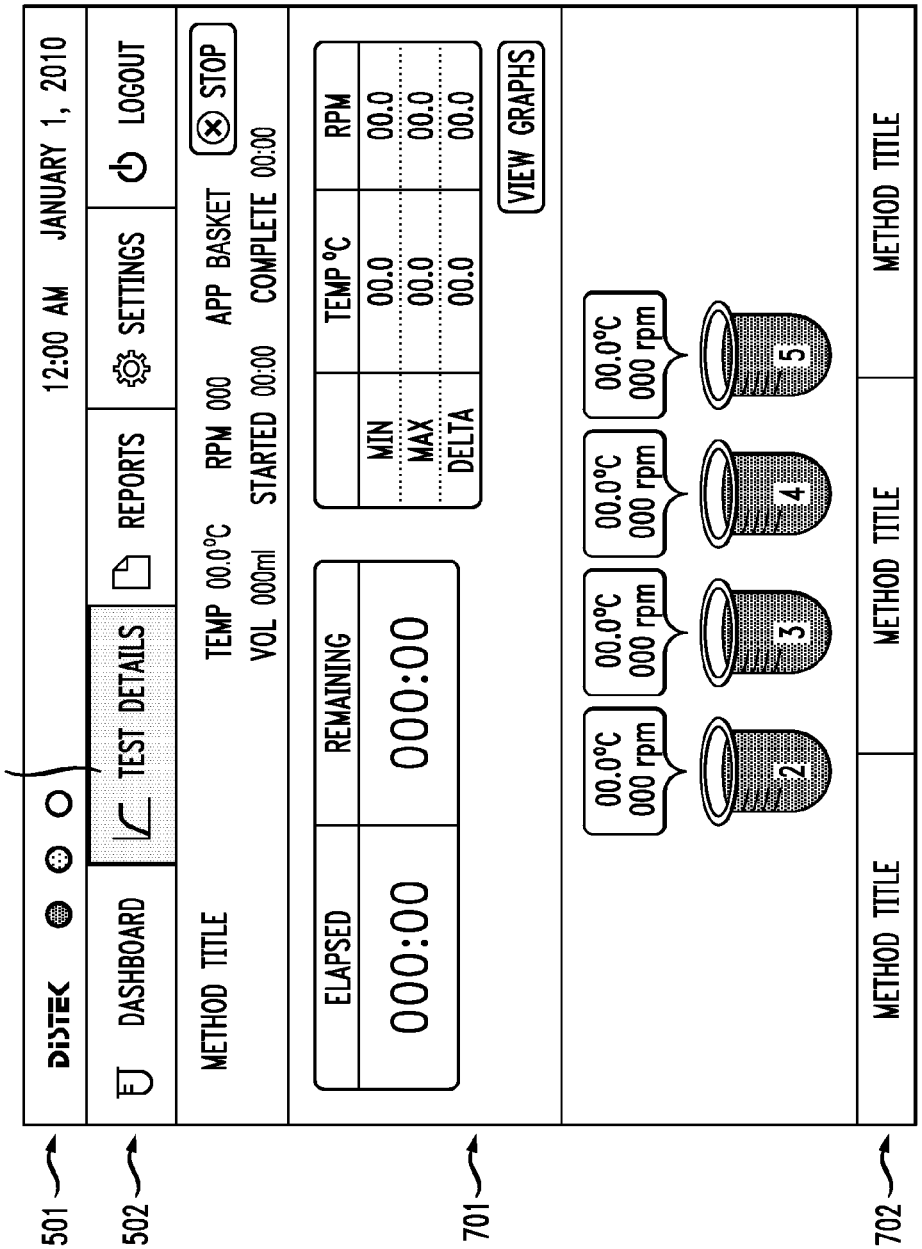
FIG. 7 shows the exemplary operations window of FIG. 5, after selecting the test-details tab.

FIG. 7 shows exemplary operations window 500 of FIG. 5, after selecting the test-details tab. Status ribbon 501 and tab-select ribbon 502 in FIG. 7 remain substantially the same as in FIG. 5, except that test-details tab 507 is shown as the selected tab. Instead of tab-info window 503, operations window 500 in FIG. 7 now shows tab-info window 701. Tab-info window 701 shows the method for the group of vessels shown as selected in FIG. 5, namely the vessels corresponding to vessel icons 2-5. Consequently, tab-info window 701 shows the vessel icons and sensed temperature and stirring speed information for only the selected vessels. Tab-info window 701 also shows the method name, target temperature and stirring speed, stirring-shaft attachment, vessel volume, start time, completion time, elapsed time, and time remaining until the next scheduled step. Tab-info window 701 also shows the minimum, maximum, and delta (e.g., the difference between the maximum and minimum values) of the sensed temperature and stirring speed. Tab-info window 701 further includes a stop button to stop the method and a view-graphics button to show graphs of the sensed temperature and stirring speed over the course of the method. At the bottom of tab-info window 701 is method-select ribbon 702, which allows switching views among a plurality of simultaneously active methods.

FIG. 8 shows exemplary operations window 500 of FIG. 5, after selecting the reports tab and a completed method. When reports tab 508 is first selected, a list of historical test methods is presented. Once one test method is selected, operations window 500 appears as in FIG. 8. Status ribbon 501 and tab-select ribbon 502 in FIG. 8 remain substantially the same as in FIG. 5, except that reports tab 508 is shown as the selected tab. Instead of tab-info window 503, operations window 500 in FIG. 8 now shows report window 801. Report window 801 shows a summary of sensed information for the vessels over a selected time range. In particular, report window 801 shows the last, minimum, maximum, and delta values of the sensed temperature and stirring speed for vessels 1-8. Report window 801 also shows a method name, target temperature, and stirring speed, as well as the attachment type, volume, start time, end time, and user identification. Report window 801 also includes print button 802 for printing reports and back button 803 for returning to the above-described method-listing window.

Report window 801 may allow a user to save reports of the sensed operational information. Report window 801 may show detailed report information instead of the above-described summary information and allow its printing and/or saving. Detailed report information would show, for selected vessels, the sensed temperature and stirring speed at particular time intervals over a particular time range.

Figure 9:
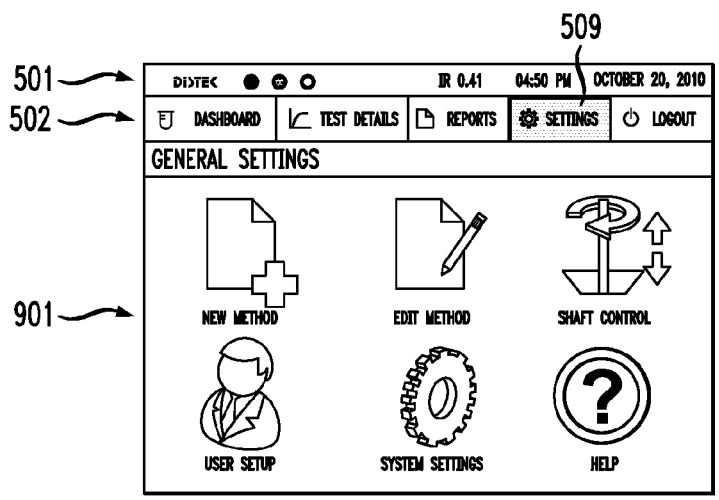
FIG. 9 shows the exemplary operations window of FIG. 5, after selecting the settings tab.

FIG. 9 shows exemplary operations window 500 of FIG. 5, after selecting the settings tab. Status ribbon 501 and tab-select ribbon 502 in FIG. 9 remain substantially the same as in FIG. 5, except that settings tab 509 is shown as the selected tab. Instead of tab-info window 503, operations window 500 in FIG. 9 now shows settings window 901. Settings window 901 has a title indicating that it is a general settings window and includes selectable icons to allow a user to: (1) create a new test method, (2) edit an existing test method, (3) manually control one or more stirring shafts, (4) view and/or change user accounts, (5) view and/or change system settings, and (6) view help information.

Selecting the edit-method icon in settings window 901 brings up an edit-method window (not shown) that allows a user to select, view, edit, and re-save already extant test methods. The controller of apparatus 100 of FIG. 1 may record the user identification, changes made, and time in order to maintain an audit trail of changes. Selecting the new-method icon in settings window 901 of FIG. 9 brings up a new-method window (not shown) that allows a user to create and save a new test method. An audit trail may be maintained for new methods as well. The new-method window allows the user to name the new method and set parameters such as target temperature, solution volume, agitator apparatus, duration, and corresponding dissolution-testing modules. The appearance and input options for the new-method window may dynamically change depending on the parameter being set. For example, a keypad may appear to enter the target temperature, a list of compatible attachments for attachment type, and a full keyboard for method name. Note that, in general, appearance and input options for any window may dynamically change depending on a variety of programmable factors. If an auto-sampler will be used as part of apparatus 100 for a test method, then auto-sampler parameters—such as, for example, sample volume, flow rate, and/or flush time—may also be specified in the edit-method and new-method windows.

Selecting the shaft-control icon in settings window 901 brings up a shaft-control window (not shown) that allows a user to manually control the operation of one or more stirring shafts. The shaft-control window allows the user to select the modules whose shafts are to be manually controlled. The shaft-control window allows the user to set, for the selected stirring shafts, stirring speed (e.g., in RPM), stirring mode (e.g., continuous or pulse), and up/down speed (e.g., slow, medium, or fast). The shaft-control window further allows the user to (1) start and stop stirring and (2) start and stop stirring-shaft ascent and descent.

Figure 10:
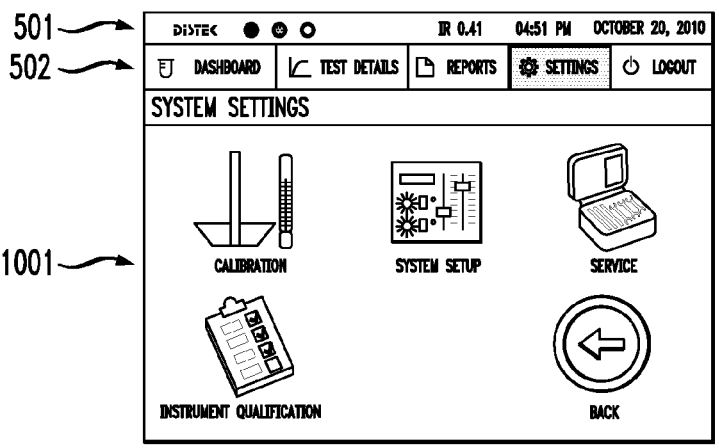
FIG. 10 shows the exemplary operations window of FIG. 9, after selecting the system-settings icon.

FIG. 10 shows exemplary operations window 500 of FIG. 9, after selecting the system-settings icon. Status ribbon 501 and tab-select ribbon 502 in FIG. 10 remain substantially the same as in FIG. 9. Instead of showing settings window 901, operations window 500 in FIG. 10 now shows system-settings window 1001. System-settings window 1001 has a title indicating that it is a systems-settings window and includes selectable icons to allow a user to: (1) calibrate components of apparatus 100 of FIG. 1—such as vessel-heating elements, (2) view and/or change setup options for apparatus 100, (3) service apparatus 100, (4) maintain instrument-qualification information (e.g., add, edit, and/or delete scheduling information regarding component maintenance), and/or (5) return to settings window 901.

Selecting the setup-options icon in system-settings window 1001 of FIG. 10 brings up a setup-options window (not shown) that allows a user to view and/or edit various system properties. User-settable system properties may include, for example, instrument name, lighting settings, presence and status of an automatic dosage-delivery system, touch screen calibration, and/or sound settings. Programming of a temperature control system (TCS) for a bath system may also be done here. The bath heater and water pump of a bath system, if used, may also be manually controlled via touch screen 115.

Certain system properties may be restricted to modification only by a qualified technician rather than by an end user. Such system properties may be set by attaching an authorized external computer to the above-noted serial communication port of base unit 101. Such system properties may include, for example, whether apparatus 100 of FIG. 1 uses a vessel bath or is bathless, which attachment bays have attached dissolution-testing modules, and/or certain properties of a bath system, if one is used.

Figure 11:
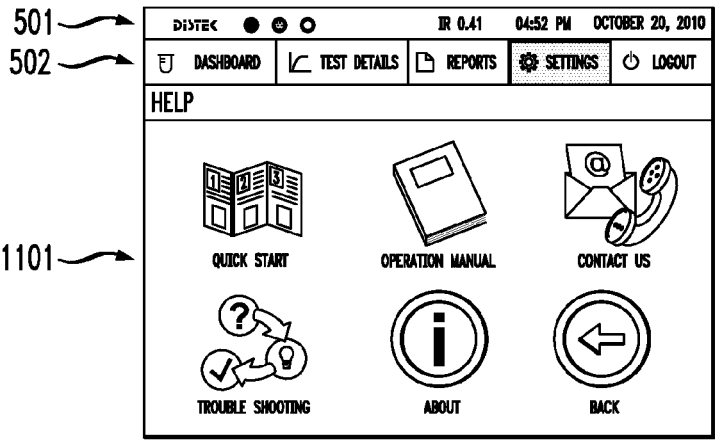
FIG. 11 shows the exemplary operations window of FIG. 9, after selecting the help icon.

FIG. 11 shows exemplary operations window 500 of FIG. 9, after having the help icon selected. Status ribbon 501 and tab-select ribbon 502 in FIG. 11 remain substantially the same as in FIG. 9. Instead of showing settings window 901, operations window 500 in FIG. 11 now shows help window 1101. Help window 1101 has a title indicating that it is a help window and includes selectable icons to allow a user to: (1) view quick-start information for apparatus 100 of FIG. 1, (2) view the operations manual for apparatus 100, (3) view contact information for the provider of apparatus 100, (4) perform trouble-shooting operations, (5) view information about apparatus 100, and/or (6) return to settings window 901.

It should be noted that various changes in the details, materials, and arrangements of the parts which have been described and illustrated in order to explain the nature of this invention may be made by those skilled in the art without departing from the scope of the invention as expressed in the following claims. Several exemplary variations are described below.

In some alternative embodiments, the clutch mechanism of multi-motion assembly 305 of FIG. 3 is set by a mechanism other than a brake pad. These embodiments do not include a brake pad and brake-pad locator 310. In some of these embodiments, the clutch shifting location is controlled by the controller of base unit 101 and may be set manually by a user or automatically by a program.

In some alternative embodiments of apparatus 100 of FIG. 1, a dissolution-testing module and/or an unused-attachment-bay cover is held in place in its corresponding attachment bay by means other than screws. In some implementations, clasps or clips secure the module to the base unit. In some implementations, magnets are used. In some implementations, guides and grooves on the module and/or corresponding attachment bay are used to slide the module into the corresponding attachment bay.

In some alternative embodiments of apparatus 100 of FIG. 1, armature 113 is connected to base unit 101 in a manner other than rotatably. For example, in one alternative implementation, armature 113 is immovably connected to base unit 101. In another implementation, armature 113 is connected to base unit 101 with a ball-and-socket connection—allowing multi-dimensional freedom of motion. In yet another implementation, armature 113 is in the form of a flexible yet sturdy tube (sometimes referred to as a "gooseneck")—also allowing multi-dimensional freedom of motion. The connection of armature 113 to user interface 114 may be similarly varied.

In an alternative embodiment of apparatus 100 of FIG. 1, dissolution-testing module 102 does not have a motor, and motive power is provided by base unit 101. Motive power is transferred to module 102 using means such as, for example, belts, gears, shafts, and/or electromagnetic propulsion.

In some alternative embodiments of apparatus 100 of FIG. 1, dissolution-testing module 102 does not include heating jacket 309. In some of the above-described alternative embodiments, as described above, vessel 308 is placed in a temperature-controlled water bath. The water bath may be a single-unit water bath or multi-unit water bath. Apparatus 100 may include a single multi-unit water bath for all attachable dissolution-testing modules (e.g., a water bath that would fit the vessels of eight dissolution-testing modules) or apparatus 100 may include one or more smaller multi-unit baths (e.g., one or more two-vessel baths). In some of the above-described alternative embodiments, apparatus 100 includes heating and regulating elements for the one or more water baths, where the heating is regulated by the controller of base unit 101.

In some embodiments, dissolution-testing module 102 of FIG. 1 comprises one or more lights (e.g., LEDs) in one or more colors. The lights may be used to illuminate the contents of the vessel. The lights may also be used to identify particular vessels for feedback to a user using touch screen 115 of FIG. 1 in order to, for example, highlight, a particular set of modules being monitored or programmed. The identification may be accomplished by using lights of substantially the same color as the color of the corresponding vessel icons on touch screen 115.

In some alternative embodiments of apparatus 100 of FIG. 1, base unit 101 has fewer or more attachment bays than eight. In some embodiments, the attachment bays are arranged in a configuration other than an arced curve. In one alternative embodiment, the attachment bays are arranged as two outward facing rows. For example, one alternative modular system has a substantially rectangular footprint and comprises four attachment bays on one side and four attachment bays on the other.

Some embodiments use one or more dissolution-testing modules that do not include an agitator apparatus or motor. These dissolution-testing modules may comprise a vessel with a heating jacket. Such modules may be a lower-cost way to provide a reservoir for replacement solvent, where replacement solvent is used to replace solution pulled during testing, as described above.

In some alternative embodiments, the controller is located inside user interface 114 of FIG. 1. In some embodiments, the controller is integrated with the user-interface controller of user interface 114. In some implementations, the controller is implemented in a distributed manner, where parts of the controller are communicatively connected together and may be located in user interface 114, base unit 101, and/or elsewhere.

In some alternative embodiments, touch screen 115 of FIG. 1 is a black and white, rather than a color, screen.

In some alternative embodiments, options on touch screen 115 of FIG. 1 that are not available at a particular operational point are not visually altered. Instead, pressing those options causes a fault alert, such as an error window popping up and/or an audible alert sounding, indicating that the selected option is not available.

In some alternative embodiments, user interface 114 of FIG. 1 comprises input devices—such as, for example, buttons, slides, and/or knobs—other than a touch screen. In some of the above-described alternative embodiments, user interface 114 does not include any touch screen. In some of the above-described alternative embodiments, user interface 114 does not include any kind of visual-output screen.

In some alternative embodiments of apparatus 100 of FIG. 1, user interface 114 is wirelessly connectable to base unit 101. In some of the above-described alternative embodiments, user interface 114 is connectable to and detachable from armature 113. In some of the above-described alternative embodiments, base unit 101 does not include an armature such as armature 113. In some alternative embodiments, user interface 114 and/or the controller may be implemented as a general-purpose computer (e.g., an iPad from Apple Inc., of Cupertino, Calif.) programmed to perform above-described interface and/or controller functions.

In some alternative embodiments of apparatus 100 of FIG. 1, the detachable modules use stirring, agitating, and/or heating mechanisms different from the ones described above.

In some alternative embodiments of detachable module 102 of FIG. 3, the medium stirred by the agitator apparatus is a medium other than a solution.

In some alternative embodiments of apparatus 100 of FIG. 2, the apparatus is an integrated system of non-detachable dissolution-testing modules. In these embodiments, the agitator apparatus of each dissolution-testing module (including its agitation parameters) remains independently controllable and, consequently, the controller remains able to simultaneously run different methods on different sets of dissolution-testing modules.

It should be noted that embodiments of the invention are not limited to dissolution-testing systems. Alternative embodiments comprise modular systems other than dissolution-testing systems. Some of these alternative embodiments are disintegration-testing or other motorized pharmaceutical systems. In disintegration testing, for example, the agitator apparatus is a reciprocating apparatus that reciprocates up and down rather than rotating as in dissolution testing. Consequently, in a disintegration-testing system, detachable module 102 of FIG. 3 has a reciprocator assembly powered by motor 302 for reciprocating the reciprocating apparatus. In addition, agitation parameters other than stirring speed may be used in disintegration-testing systems. For example, agitation parameters for a test method in a disintegration-testing system may include reciprocations per minute instead of revolutions per minute.

Some other of these alternative embodiments may be non-pharmaceutical motorized, modular, and scalable scientific instrumentation systems. Some of these alternative embodiments comprise a system having a central controller, base unit, and two or more attachment bays for one or more motorized modules, where the central controller receives input from, and controls operation of, the motorized modules.

References herein to the verb "to set" and its variations in reference to values of fields do not necessarily require an active step and may include leaving a field value unchanged if its previous value is the desired value. Setting a value may nevertheless include performing an active step even if the previous or default value is the desired value.

Unless indicated otherwise, the term "determine" and its variants as used herein refer to obtaining a value through measurement and, if necessary, transformation. For example, to determine an electrical-current value, one may measure a voltage across a current-sense resistor, and then multiply the measured voltage by an appropriate value to obtain the electrical-current value. If the voltage passes through a voltage divider or other voltage-modifying components, then appropriate transformations can be made to the measured voltage to account for the voltage modifications of such components and to obtain the corresponding electrical-current value.

As used herein in reference to data transfers between entities in the same device, and unless otherwise specified, the terms "receive" and its variants can refer to receipt of the actual data, or the receipt of one or more pointers to the actual data, wherein the receiving entity can access the actual data using the one or more pointers.

Exemplary embodiments have been described wherein particular entities (a.k.a. modules) perform particular functions. However, the particular functions may be performed by any suitable entity and are not restricted to being performed by the particular entities named in the exemplary embodiments.

The present invention may be implemented as circuit-based systems, including possible implementation as a single integrated circuit (such as an ASIC or an FPGA), a multi-chip module, a single card, or a multi-card circuit pack. As would be apparent to one skilled in the art, various functions of circuit elements may also be implemented as processing steps in a software program. Such software may be employed in, for example, a digital signal processor, micro-controller, or general-purpose computer.

The present invention can be embodied in the form of methods and apparatuses for practicing those methods. The present invention can also be embodied in the form of program code embodied in tangible media, such as magnetic recording media, optical recording media, solid state memory, floppy diskettes, CD-ROMs, hard drives, or any other non-transitory machine-readable storage medium, wherein, when the program code is loaded into and executed by a machine, such as a computer, the machine becomes an apparatus for practicing the invention. The present invention can also be embodied in the form of program code, for example, stored in a non-transitory machine-readable storage medium including being loaded into and/or executed by a machine, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Unless explicitly stated otherwise, each numerical value and range should be interpreted as being approximate as if the word "about" or "approximately" preceded the value of the value or range. As used in this application, unless otherwise explicitly indicated, the term "connected" is intended to cover both direct and indirect connections between elements.

For purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. The terms "directly coupled," "directly connected," etc., imply that the connected elements are either contiguous or connected via a conductor for the transferred energy.

The use of figure numbers and/or figure reference labels in the claims is intended to identify one or more possible embodiments of the claimed subject matter in order to facilitate the interpretation of the claims. Such use is not to be construed as limiting the scope of those claims to the embodiments shown in the corresponding figures.

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

Although the steps in the following method claims are recited in a particular sequence with corresponding labeling, unless the claim recitations otherwise imply a particular sequence for implementing some or all of those steps, those steps are not necessarily intended to be limited to being implemented in that particular sequence.

We claim:

1. A detachable module usable for scientific testing, the detachable module adapted to attach to, and detach from, a corresponding attachment bay of a base unit, wherein:

the base unit comprises a controller; and the detachable module comprises:
a first connection port adapted to support communication with the controller, the first connection port adapted to connect to a corresponding connection port of the corresponding attachment bay when the detachable module is attached to the base unit;
a first sensor adapted to provide a first output to the controller via the first connection port; and
an agitator apparatus adapted to:
agitate a medium; and
be controlled by the controller via the first connection port.

2. The detachable module of claim 1, wherein the detachable module is adapted to be configured with a vessel for holding the medium to be agitated by the agitator apparatus.

3. The detachable module of claim 1, wherein:
the detachable module further comprises an electric heater adapted to heat the medium; and
the controller is adapted to control the electric heater, via the first communication port, based on the first output so as to maintain the medium at a target temperature.

4. The detachable module of claim 3, wherein the electric heater is a heating jacket directly attached to the vessel.

5. The detachable module of claim 1, wherein:
the sensor is a temperature sensor adapted to sense a temperature of the medium; and
the first output indicates the sensed temperature.

6. The detachable module of claim 1, wherein:
the module comprises a stirring shaft;
the agitator apparatus is adapted to attach to and be rotated by the stirring shaft; and
the agitator apparatus is one of a paddle and a basket.

7. The detachable module of claim 6, wherein the sensor is located within the stirring shaft.

8. The detachable module of claim 1, wherein the agitator apparatus is a reciprocating apparatus.

9. The detachable module of claim 1, wherein:
the detachable module further comprises an electric motor adapted to be communicatively connected to the controller via the first connection port;
the electric motor is adapted to be controlled by the controller; and
the electric motor is adapted to provide power for agitation of the medium by the agitator apparatus.

10. The detachable module of claim 9, wherein:
the module further comprises a stirring shaft;
the agitator apparatus is adapted to attach to and be rotated by the stirring shaft;
the module comprises a multi-motion assembly connected between the electric motor and the stirring shaft; and
the multi-motion assembly allows the electric motor to:
rotate the stirring shaft without lowering or raising the stirring shaft;
lower the stirring shaft without rotating the stirring shaft; and
raise the stirring shaft without rotating the stirring shaft.

11. The detachable module of claim 1, wherein the detachable module is adapted to:
be uniquely identifiable by a unique identification code; and
provide the unique identification code to the controller via the first connection port.

12. An apparatus usable for scientific testing, the apparatus comprising a base unit comprising:
a plurality of attachment bays;
a user interface; and
a controller communicatively connected to the user interface, wherein each of the plurality of attachment bays:
(a) is adapted to have a corresponding detachable module attach to, and detach from, the attachment bay; and
(b) comprises a first connection port adapted to:
(i) connect to a corresponding connection port of the corresponding detachable module;
(ii) support communication between the corresponding detachable module and the controller when the corresponding detachable module is attached to the attachment bay;
(iii) transmit a first output from a sensor in the corresponding detachable module to the controller; and
(iv) support control by the controller of an agitator apparatus in the corresponding detachable module, wherein the agitator apparatus is adapted to agitate a medium.

13. The apparatus of claim 12, wherein the controller is programmable by a user via the user interface.

14. The apparatus of claim 12, wherein:
the user interface is movably connected to the base unit; and
the user interface comprises a touch screen adapted to receive touch input from a user and provide visual output to the user.

15. The apparatus of claim 12, wherein the controller is adapted to:
detect which one or more of the plurality of attachment bays have a corresponding detachable module attached; and
automatically run a reconfiguration procedure adapted to reconfigure operation of the apparatus if the controller detects that one or more detachable modules have been attached or detached.

16. The apparatus of claim 12, wherein the controller is adapted to simultaneously:
provide a first set of control instructions to a first set of one or more detachable modules attached to a corresponding first set of attachment bays of the plurality of attachment bays; and
provide a second set of control instructions, different from the first set of control instructions, to a second set of one or more detachable modules, different from the first set of one or more detachable modules, attached to a corresponding second set of attachment bays of the plurality of attachment bays, different from the first set of attachment bays.

17. The apparatus of claim 12, wherein the controller is adapted to simultaneously run at least two different test methods on at least two different corresponding sets of one or more detachable modules attached to corresponding sets of one or more attachment bays of the plurality of attachment bays, wherein running a test method comprises, for the controller and each detachable module:
receiving, by the controller, the first output indicating a temperature of a medium in a vessel of the detachable module;
controlling heating of the medium based on the first output so as to maintain the medium at a target temperature;
lowering the agitator apparatus at each of a corresponding set of one or more apparatus-lowering times;
raising the agitator apparatus at each of a corresponding set of one or more apparatus-raising times; and
agitating the medium using the agitator apparatus in accordance with a set of agitation parameters at each of a corresponding set of one or more agitation times.

18. The apparatus of claim 12, wherein the controller is further adapted to:
- receive, from each attached detachable module, a second output comprising agitator-parameter feedback for the agitator apparatus of the corresponding detachable module;
- record, for each attached detachable module, a first value corresponding to the first output and a second value corresponding to the second output for each of a set of one or more recording times; and
- output a table of the recorded times, corresponding first values, and corresponding second values for each attached detachable module.

19. The apparatus of claim 12, further comprising one or more attached detachable modules.

20. A method for scientific testing using an apparatus, wherein:
- the apparatus comprises a first detachable module and a base unit;
- the first detachable module comprises:
  - (a) a sensor;
  - (b) an agitator apparatus adapted to agitate a medium; and
  - (c) a first connection port;
- the base unit comprises:
  - (a) a plurality of attachment bays;
  - (b) a user interface; and
  - (c) a controller communicatively connected to the user interface, wherein each of the plurality of attachment bays:
    - (i) is adapted to have a corresponding detachable module attach to or detach from the attachment bay; and
    - (ii) comprises a corresponding connection port;
- the first detachable module is attached to a first attachment bay of the plurality of attachment bays; and
- the first connection port of the first detachable module is connected to the corresponding connection port of the first attachment bay, wherein the method comprises:
  - (a) communicating, by the controller, with the first detachable module via the first connection port;
  - (b) receiving, by the controller, a first output from the sensor in the first detachable module; and
  - (c) controlling, by the controller, of the agitator apparatus in the first detachable module.

21. An apparatus usable for scientific testing, the apparatus comprising:
- a user interface;
- a controller communicatively connected to the user interface; and
- a plurality of testing modules, each of the plurality of testing modules comprising:
  - a first sensor adapted to provide a first output to the controller; and
  - an agitator apparatus adapted to:
    - agitate a medium; and
    - be controlled by the controller, wherein the controller is adapted to simultaneously:
      - provide a first set of control instructions to a first set of one or more of the plurality of testing modules; and
      - provide a second set of control instructions, different from the first set of control instructions, to a second set of one or more of the plurality of testing modules, different from the first set of one or more of the plurality of testing modules.

* * * * *